United States Patent
Dominguez (10) Patent No.: US 8,920,447 B2
(45) Date of Patent: Dec. 30, 2014

(54) ARTICULATED GASTRIC IMPLANT CLIP

(75) Inventor: Zachary Dominguez, Santa Barbara, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 235 days.

(21) Appl. No.: 13/272,083

(22) Filed: Oct. 12, 2011

(65) Prior Publication Data
US 2012/0095484 A1    Apr. 19, 2012

Related U.S. Application Data (60) Provisional application No. 61/485,009, filed on May 11, 2011, provisional application No. 61/394,592, filed on Oct. 19, 2010.

(51) Int. Cl.
*A61B 17/08*    (2006.01)
*A61F 5/00*    (2006.01)

(52) U.S. Cl.
CPC ............ *A61F 5/0076* (2013.01); *A61F 5/0036* (2013.01); *A61F 5/0086* (2013.01); *A61F 5/0089* (2013.01)
USPC ............ 606/157; 606/120; 606/142; 24/495; 24/517; 24/521

(58) Field of Classification Search
CPC ... A61F 5/0036; A61F 5/0086; A61F 5/0076; A61F 5/0089; A61B 17/08
USPC ......... 606/151, 157, 153, 120, 136, 142, 154, 606/158, 201, 213, 214, 215; 600/37; 623/23.65; 24/495, 517, 521; D28/10, D28/39–43; 604/250
See application file for complete search history.

(56) References Cited

U.S. PATENT DOCUMENTS 1,702,974 A    2/1929    MacDonald
2,087,604 A *  7/1937    Mosher ........................ 132/244
(Continued)

FOREIGN PATENT DOCUMENTS

CN    1250382 A    4/2000
CN    1367670 A    9/2002
(Continued)

OTHER PUBLICATIONS

Xanthakos et al.; 'Bariatric Surgery for Extreme Adolescent Obesity: Indications, Outcomes, and Physiologic Effects on the Gut-Brain Axis'; Pathophysiology; V. 15; pp. 135-146; 2008.
(Continued)

*Primary Examiner* — Tuan V Nguyen
*Assistant Examiner* — Tin Nguyen
(74) *Attorney, Agent, or Firm* — Gordon & Jacobson, PC (57) ABSTRACT

Intragastric implant devices for obesity treatment are disclosed. The device is passive and does not autonomously change shape, but instead reacts to movement of the stomach to induce satiety. The device includes a series of connected, articulated clips that plicate the stomach wall nondestructively (no puncturing through the gastric wall) such that the overall volume of the stomach is reduced. Cam-shaped clamping surfaces prevent slippage of the stomach tissue from within the clips. Methods of implant are disclosed including delivering the device through a transoral delivery tube and advancing the device through the esophagus to be deployed within the stomach. Removal of the device occurs in the reverse.

21 Claims, 3 Drawing Sheets

(56) References Cited

U.S. PATENT DOCUMENTS

| | | | |
|---|---|---|---|
| 2,163,048 A | 6/1939 | McKee | |
| 2,619,138 A * | 11/1952 | Marler | 81/382 |
| 3,667,081 A | 6/1972 | Burger | |
| 3,719,973 A | 3/1973 | Bell | |
| 3,840,018 A | 10/1974 | Heifetz | |
| 3,919,724 A | 11/1975 | Sanders | |
| 4,118,805 A | 10/1978 | Reimels | |
| 4,364,379 A | 12/1982 | Finney | |
| 4,416,267 A | 11/1983 | Garren et al. | |
| 4,430,392 A | 2/1984 | Kelley | |
| 4,485,805 A | 12/1984 | Foster | |
| 4,545,367 A | 10/1985 | Tucci | |
| 4,586,501 A * | 5/1986 | Claracq | 606/158 |
| 4,592,355 A | 6/1986 | Antebi | |
| 4,598,699 A | 7/1986 | Garren | |
| 4,607,618 A | 8/1986 | Angelchik | |
| 4,636,213 A | 1/1987 | Pakiam | |
| 4,648,383 A | 3/1987 | Angelchik | |
| 4,694,827 A | 9/1987 | Weiner | |
| 4,723,547 A | 2/1988 | Kullas | |
| 4,739,758 A | 4/1988 | Lai et al. | |
| 4,773,432 A | 9/1988 | Rydell | |
| 4,774,956 A | 10/1988 | Kruse et al. | |
| 4,844,068 A | 7/1989 | Arata et al. | |
| 4,881,939 A | 11/1989 | Newman | |
| 4,899,747 A | 2/1990 | Garren et al. | |
| 4,925,446 A | 5/1990 | Garay et al. | |
| 4,930,535 A | 6/1990 | Rinehold | |
| 4,950,258 A | 8/1990 | Kawai | |
| 4,969,899 A | 11/1990 | Cox | |
| 5,074,868 A | 12/1991 | Kuzmak | |
| 5,084,061 A | 1/1992 | Gau | |
| 5,211,371 A | 5/1993 | Coffee | |
| 5,226,429 A | 7/1993 | Kuzmak | |
| 5,255,690 A | 10/1993 | Keith | |
| 5,259,399 A | 11/1993 | Brown | |
| 5,289,817 A | 3/1994 | Williams | |
| 5,308,324 A | 5/1994 | Hammerslag | |
| 5,312,343 A | 5/1994 | Krog et al. | |
| 5,449,368 A | 9/1995 | Kuzmak | |
| 5,514,176 A | 5/1996 | Bosley | |
| 5,527,340 A | 6/1996 | Vogel | |
| 5,540,701 A | 7/1996 | Sharkey | |
| 5,547,458 A | 8/1996 | Ortiz | |
| 5,601,604 A | 2/1997 | Vincent | |
| 5,658,298 A | 8/1997 | Vincent | |
| 5,693,014 A | 12/1997 | Abele | |
| 5,725,507 A | 3/1998 | Petrick | |
| 5,748,200 A | 5/1998 | Funahashi | |
| 5,776,160 A | 7/1998 | Pasricha | |
| 5,819,749 A | 10/1998 | Lee | |
| 5,820,584 A | 10/1998 | Crabb | |
| RE36,176 E | 3/1999 | Kuzmak | |
| 5,938,669 A | 8/1999 | Klaiber | |
| 6,074,341 A | 6/2000 | Anderson | |
| 6,102,678 A | 8/2000 | Peclat | |
| 6,102,897 A | 8/2000 | Lang | |
| 6,102,922 A | 8/2000 | Jakobsson | |
| 6,152,922 A | 11/2000 | Ouchi | |
| 6,183,492 B1 | 2/2001 | Hart | |
| 6,264,700 B1 | 7/2001 | Kilcoyne et al. | |
| 6,290,575 B1 | 9/2001 | Shipp | |
| 6,322,538 B1 | 11/2001 | Elbert et al. | |
| 6,450,946 B1 | 9/2002 | Forsell | |
| 6,454,699 B1 | 9/2002 | Forsell | |
| 6,454,785 B2 | 9/2002 | De Hoyos Garza | |
| 6,464,628 B1 | 10/2002 | Forsell | |
| 6,470,892 B1 | 10/2002 | Forsell | |
| 6,503,264 B1 | 1/2003 | Birk | |
| 6,511,490 B2 | 1/2003 | Robert | |
| 6,540,789 B1 | 4/2003 | Silverman et al. | |
| 6,547,801 B1 | 4/2003 | Dargent | |
| 6,579,301 B1 | 6/2003 | Bales et al. | |
| 6,629,776 B2 | 10/2003 | Bell | |
| 6,675,809 B2 | 1/2004 | Stack et al. | |
| 6,682,473 B1 | 1/2004 | Matsuura | |
| 6,733,512 B2 | 5/2004 | McGhan | |
| 6,733,513 B2 | 5/2004 | Boyle | |
| 6,746,460 B2 | 6/2004 | Gannoe | |
| 6,776,783 B1 * | 8/2004 | Frantzen et al. | 606/151 |
| 6,840,257 B2 | 1/2005 | Dario | |
| 6,845,776 B2 | 1/2005 | Stack et al. | |
| 6,905,471 B2 | 6/2005 | Leivseth | |
| 6,960,233 B1 | 11/2005 | Berg | |
| 6,981,978 B2 | 1/2006 | Gannoe | |
| 6,981,980 B2 | 1/2006 | Sampson et al. | |
| 6,994,095 B2 | 2/2006 | Burnett | |
| 7,008,419 B2 | 3/2006 | Shadduck | |
| 7,020,531 B1 | 3/2006 | Colliou | |
| 7,033,384 B2 | 4/2006 | Gannoe et al. | |
| 7,037,344 B2 | 5/2006 | Kagan et al. | |
| 7,056,305 B2 | 6/2006 | Garza Alvarez | |
| 7,090,699 B2 | 8/2006 | Geitz | |
| 7,214,233 B2 | 5/2007 | Gannoe et al. | |
| 7,220,237 B2 | 5/2007 | Gannoe et al. | |
| 7,220,284 B2 | 5/2007 | Kagan et al. | |
| 7,223,277 B2 | 5/2007 | DeLegge | |
| 7,320,696 B2 | 1/2008 | Gazi et al. | |
| 7,347,875 B2 | 3/2008 | Levine et al. | |
| 7,354,454 B2 | 4/2008 | Stack et al. | |
| 7,476,256 B2 | 1/2009 | Meade et al. | |
| 7,510,559 B2 | 3/2009 | Deem et al. | |
| 7,608,114 B2 | 10/2009 | Levine et al. | |
| 7,628,442 B1 * | 12/2009 | Spencer et al. | 296/100.07 |
| 7,682,330 B2 | 3/2010 | Meade et al. | |
| 7,695,446 B2 | 4/2010 | Levine et al. | |
| 7,699,863 B2 | 4/2010 | Marco et al. | |
| 7,753,870 B2 | 7/2010 | Demarais et al. | |
| 7,771,382 B2 | 8/2010 | Levine et al. | |
| 7,794,447 B2 | 9/2010 | Dann et al. | |
| 7,815,589 B2 | 10/2010 | Meade et al. | |
| 7,837,643 B2 | 11/2010 | Levine et al. | |
| 7,841,503 B2 | 11/2010 | Sonnenschein et al. | |
| 7,883,525 B2 | 2/2011 | DeLegge | |
| 7,931,693 B2 | 4/2011 | Binmoeller | |
| 7,981,162 B2 | 7/2011 | Stack et al. | |
| 8,029,455 B2 | 10/2011 | Stack et al. | |
| 8,032,223 B2 | 10/2011 | Imran | |
| 8,075,582 B2 | 12/2011 | Lointier | |
| 8,162,969 B2 | 4/2012 | Brister | |
| 8,187,297 B2 | 5/2012 | Makower | |
| 8,216,266 B2 | 7/2012 | Hively | |
| 2002/0019577 A1 | 2/2002 | Arabia | |
| 2002/0055757 A1 | 5/2002 | Torre | |
| 2002/0095181 A1 | 7/2002 | Beyar | |
| 2002/0139208 A1 | 10/2002 | Yatskov | |
| 2002/0183782 A1 | 12/2002 | Tsugita | |
| 2003/0045896 A1 | 3/2003 | Murphy | |
| 2003/0073880 A1 | 4/2003 | Polsky | |
| 2003/0074054 A1 | 4/2003 | Duerig | |
| 2003/0100822 A1 | 5/2003 | Lew | |
| 2003/0106761 A1 | 6/2003 | Taylor | |
| 2003/0109935 A1 | 6/2003 | Geitz | |
| 2003/0144575 A1 | 7/2003 | Forsell | |
| 2003/0153905 A1 | 8/2003 | Edwards et al. | |
| 2003/0158570 A1 | 8/2003 | Ferrazzi | |
| 2004/0044357 A1 | 3/2004 | Gannoe et al. | |
| 2004/0092892 A1 | 5/2004 | Kagan et al. | |
| 2004/0117031 A1 | 6/2004 | Stack et al. | |
| 2004/0122452 A1 | 6/2004 | Deem et al. | |
| 2004/0122453 A1 | 6/2004 | Deem et al. | |
| 2004/0143342 A1 | 7/2004 | Stack | |
| 2004/0148034 A1 | 7/2004 | Kagan | |
| 2004/0172142 A1 | 9/2004 | Stack | |
| 2004/0186503 A1 | 9/2004 | DeLegge | |
| 2005/0033332 A1 | 2/2005 | Burnett | |
| 2005/0049718 A1 | 3/2005 | Dann et al. | |
| 2005/0055039 A1 | 3/2005 | Burnett et al. | |
| 2005/0085923 A1 | 4/2005 | Levine et al. | |
| 2005/0096692 A1 | 5/2005 | Linder et al. | |
| 2005/0110280 A1 | 5/2005 | Guy | |
| 2005/0131485 A1 | 6/2005 | Knudson | |
| 2005/0190070 A1 | 9/2005 | Rudduck | |
| 2005/0192614 A1 | 9/2005 | Binmoeller | |

(56) References Cited

U.S. PATENT DOCUMENTS

| | | |
|---|---|---|
| 2005/0192615 A1 | 9/2005 | Torre |
| 2005/0197714 A1 | 9/2005 | Sayet |
| 2005/0228504 A1 | 10/2005 | Demarais |
| 2005/0240279 A1 | 10/2005 | Kagan |
| 2005/0250979 A1 | 11/2005 | Coe |
| 2005/0256533 A1* | 11/2005 | Roth et al. .................... 606/167 |
| 2005/0261711 A1 | 11/2005 | Okada |
| 2005/0267595 A1 | 12/2005 | Chen et al. |
| 2005/0267596 A1 | 12/2005 | Chen et al. |
| 2005/0273060 A1 | 12/2005 | Levy et al. |
| 2005/0277975 A1 | 12/2005 | Saadat |
| 2006/0020278 A1 | 1/2006 | Burnett |
| 2006/0025799 A1 | 2/2006 | Basu |
| 2006/0069403 A1 | 3/2006 | Shalon |
| 2006/0106288 A1 | 5/2006 | Roth |
| 2006/0142700 A1 | 6/2006 | Sobelman |
| 2006/0178691 A1 | 8/2006 | Binmoeller |
| 2006/0190019 A1 | 8/2006 | Gannoe |
| 2006/0217762 A1 | 9/2006 | Maahs |
| 2006/0229702 A1 | 10/2006 | Agnew |
| 2006/0252983 A1 | 11/2006 | Lembo et al. |
| 2007/0010864 A1 | 1/2007 | Dann et al. |
| 2007/0016262 A1 | 1/2007 | Gross et al. |
| 2007/0021761 A1* | 1/2007 | Phillips .................... 606/157 |
| 2007/0078476 A1 | 4/2007 | Hull, Sr. et al. |
| 2007/0083224 A1 | 4/2007 | Hively |
| 2007/0100368 A1 | 5/2007 | Quijano et al. |
| 2007/0118168 A1 | 5/2007 | Lointier et al. |
| 2007/0135803 A1 | 6/2007 | Belson |
| 2007/0135829 A1 | 6/2007 | Paganon |
| 2007/0147170 A1 | 6/2007 | Hood |
| 2007/0149994 A1 | 6/2007 | Sosnowski |
| 2007/0156013 A1 | 7/2007 | Birk |
| 2007/0156248 A1 | 7/2007 | Marco |
| 2007/0173881 A1 | 7/2007 | Birk et al. |
| 2007/0185374 A1 | 8/2007 | Kick |
| 2007/0185375 A1 | 8/2007 | Kick et al. |
| 2007/0239284 A1 | 10/2007 | Skerven et al. |
| 2007/0250020 A1 | 10/2007 | Kim |
| 2007/0265598 A1 | 11/2007 | Karasik |
| 2007/0276428 A1 | 11/2007 | Haller |
| 2007/0288033 A1 | 12/2007 | Murature |
| 2007/0293716 A1 | 12/2007 | Baker et al. |
| 2008/0015618 A1 | 1/2008 | Sonnenschein et al. |
| 2008/0058840 A1 | 3/2008 | Albrecht et al. |
| 2008/0058887 A1 | 3/2008 | Griffin et al. |
| 2008/0065122 A1 | 3/2008 | Stack |
| 2008/0071305 A1 | 3/2008 | DeLegge |
| 2008/0097513 A1 | 4/2008 | Kaji et al. |
| 2008/0167606 A1 | 7/2008 | Dann |
| 2008/0172079 A1 | 7/2008 | Birk |
| 2008/0208240 A1 | 8/2008 | Paz |
| 2008/0208241 A1 | 8/2008 | Weiner et al. |
| 2008/0221595 A1 | 9/2008 | Surti |
| 2008/0228205 A1 | 9/2008 | Sharkey |
| 2008/0234718 A1 | 9/2008 | Paganon et al. |
| 2008/0234834 A1 | 9/2008 | Meade et al. |
| 2008/0243071 A1 | 10/2008 | Quijano |
| 2008/0243166 A1 | 10/2008 | Paganon et al. |
| 2008/0249635 A1 | 10/2008 | Weitzner et al. |
| 2008/0255601 A1 | 10/2008 | Birk |
| 2008/0255678 A1 | 10/2008 | Cully et al. |
| 2008/0262529 A1 | 10/2008 | Jacques |
| 2008/0306506 A1 | 12/2008 | Leatherman |
| 2009/0012553 A1 | 1/2009 | Swain et al. |
| 2009/0082644 A1 | 3/2009 | Li |
| 2009/0093767 A1 | 4/2009 | Kelleher |
| 2009/0093837 A1 | 4/2009 | Dillon |
| 2009/0131968 A1 | 5/2009 | Birk |
| 2009/0132031 A1 | 5/2009 | Cook |
| 2009/0149879 A1 | 6/2009 | Dillon |
| 2009/0177215 A1 | 7/2009 | Stack |
| 2009/0198210 A1 | 8/2009 | Burnett et al. |
| 2009/0216337 A1 | 8/2009 | Egan |
| 2009/0259246 A1 | 10/2009 | Eskaros et al. |
| 2009/0275973 A1 | 11/2009 | Chen et al. |
| 2009/0287231 A1 | 11/2009 | Brooks et al. |
| 2009/0299327 A1 | 12/2009 | Tilson |
| 2009/0299486 A1 | 12/2009 | Shohat et al. |
| 2009/0312597 A1* | 12/2009 | Bar et al. .................... 600/37 |
| 2010/0030017 A1 | 2/2010 | Baker et al. |
| 2010/0049224 A1 | 2/2010 | Vargas |
| 2010/0081991 A1 | 4/2010 | Swisher |
| 2010/0082047 A1* | 4/2010 | Cosgrove et al. .............. 606/151 |
| 2010/0087843 A1 | 4/2010 | Bertolote |
| 2010/0100079 A1 | 4/2010 | Berkcan |
| 2010/0100115 A1 | 4/2010 | Soetermans et al. |
| 2010/0121371 A1 | 5/2010 | Brooks et al. |
| 2010/0168782 A1 | 7/2010 | Hancock |
| 2010/0168783 A1 | 7/2010 | Murature |
| 2010/0174307 A1 | 7/2010 | Birk |
| 2010/0198249 A1 | 8/2010 | Sabliere |
| 2010/0234937 A1 | 9/2010 | Wang |
| 2010/0249822 A1 | 9/2010 | Nihalani |
| 2010/0249825 A1 | 9/2010 | Nihalani |
| 2010/0256775 A1 | 10/2010 | Belhe et al. |
| 2010/0256776 A1 | 10/2010 | Levine et al. |
| 2010/0261390 A1* | 10/2010 | Gardner et al. .............. 439/775 |
| 2010/0274194 A1 | 10/2010 | Sobelman |
| 2010/0286628 A1 | 11/2010 | Gross |
| 2010/0305590 A1 | 12/2010 | Holmes et al. |
| 2010/0331756 A1 | 12/2010 | Meade et al. |
| 2010/0332000 A1 | 12/2010 | Forsell |
| 2011/0009897 A1 | 1/2011 | Forsell |
| 2011/0106113 A1 | 5/2011 | Tavakkolizadeh |
| 2011/0307075 A1 | 12/2011 | Sharma |
| 2012/0022561 A1 | 1/2012 | Forsell |
| 2012/0095483 A1 | 4/2012 | Babkes |
| 2012/0221037 A1 | 8/2012 | Birk |

FOREIGN PATENT DOCUMENTS

| | | |
|---|---|---|
| DE | 8804765 U1 | 5/1989 |
| DE | 102007025312 | 11/2008 |
| EP | 1396242 A1 | 3/2004 |
| EP | 1396243 A1 | 3/2004 |
| EP | 1397998 | 3/2004 |
| EP | 1774929 | 4/2007 |
| EP | 2095798 | 9/2009 |
| FR | 2797181 A1 | 2/2001 |
| FR | 2823663 A1 | 10/2002 |
| FR | 2852821 A1 | 10/2004 |
| FR | 2855744 A1 | 12/2004 |
| FR | 2892297 | 4/2007 |
| FR | 2941617 | 8/2010 |
| GB | 2086792 A | 5/1982 |
| JP | S63279854 A | 11/1988 |
| JP | 1049572 A | 2/1989 |
| JP | 63264078 | 10/1998 |
| WO | 8800027 | 1/1988 |
| WO | WO 88/00027 | 1/1988 |
| WO | 0015158 A1 | 3/2000 |
| WO | 0032092 | 6/2000 |
| WO | 0110359 A1 | 2/2001 |
| WO | 0149245 A2 | 7/2001 |
| WO | 0166166 A2 | 9/2001 |
| WO | 0235980 A2 | 5/2002 |
| WO | 03055419 A1 | 7/2003 |
| WO | 03105732 A1 | 12/2003 |
| WO | 2004019671 A2 | 3/2004 |
| WO | 2005007231 A1 | 1/2005 |
| WO | 2005094257 | 10/2005 |
| WO | 2005097012 | 10/2005 |
| WO | WO 2005/097012 | 10/2005 |
| WO | 2005110280 | 11/2005 |
| WO | WO 2005/110280 | 11/2005 |
| WO | 2006044640 | 4/2006 |
| WO | 2006020370 | 6/2006 |
| WO | 2006063593 A2 | 6/2006 |
| WO | 2006090018 A1 | 8/2006 |
| WO | WO 2006/111961 | 10/2006 |
| WO | WO 2006/118744 | 11/2006 |
| WO | WO 2007/027812 | 3/2007 |
| WO | WO 2007053556 | 5/2007 |

(56) References Cited

FOREIGN PATENT DOCUMENTS

| WO | 2007076021 | 7/2007 |
| WO | WO 2007/092390 | 8/2007 |
| WO | WO 2007/110866 | 10/2007 |
| WO | 2008101048 | 8/2008 |
| WO | WO 2008/112894 | 9/2008 |
| WO | WO 2008/132745 | 11/2008 |
| WO | WO 2010/042062 | 4/2010 |
| WO | 2010074712 | 7/2010 |
| WO | WO 2010/074712 | 7/2010 |
| WO | WO 2010/087757 | 8/2010 |
| WO | WO 2010/117641 | 10/2010 |

OTHER PUBLICATIONS

Baggio et al. 'Biology of Integrins: GLP-1 and GIP'; Gastroenrology; V. 132; pp. 2131-2157; 2007.

Berne et al; 'Physiology'; V. 5; pp. 55-57, 210, 428, 540, 554, 579, 584, 591; 2004.

Boulant et al.; 'Cholecystokinin in Transient Lower Oesophageal Sphincter Relation Due to Gastric Distension in Humans'; Gut; V. 40; pp. 575-581; 1997.

Bradjewin et al; 'Dose Ranging Study of the Effects of Cholecystokinin in Healthy Volunteers'; J. Psychiatr. Neurosci.; V. 16 (2); pp. 91-95; 1991.

Chaudhri; 'Can Gut Hormones Control Appetite and Prevent Obesity?' Diabetes Care; V. 31; Supp 2; pp. S284-S289; Feb. 2008.

Cohen et al.; 'Oxyntomodulin Suppresses Appetite and Reduces Food in Humans'; J. Clin. Endocrinol. Metab.; V. 88; pp. 4696-4701; 2003.

Dakin et al.; 'Oxyntomodulin Inhibits Food Intake in the Rat'; Endocrinology; V. 142; pp. 4244-4250; 2001.

Dakin et al.; 'Peripheral Oxyntomodulin Reduces Food Intake and Body Weight gain in Rats'; Endocrinology; V. 145; No. 6; pp. 2687-2695; Jun. 2004.

Davison; 'Activation of Vagal-Gastric Mechanoreceptors by Cholecystokinin'; Proc. West. Pharmacol. Soc; V. 29; pp. 363-366; 1986.

Ekblad et al.; 'Distribution of Pancreatic Peptide and Peptide-YY'; Peptides; V. 23; pp. 251-261;2002.

Greenough et al.; 'Untangling the Effects of Hunger, Anxiety and Nausea on Energy Intake During Intravenous Cholecystokinin Octapeptide (CCK-8) Infusion' Physiology and Behavior; V. 65 (2); pp. 303-310; 1998.

Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.

Houpt; 'Gastrointestinal Factors in Hunger and Satiety'; Neurosci. and Behav. Rev.; V. 6; pp. 145-164; 1982.

Kissileff et al.; 'Peptides that Regulate Food Intake: Cholecystokinin and Stomach Distension Combine to Reduce Food Intake in Humans'; Am. J. Physiol. Regul. Integr. Comp. Physiol.; V. 285; pp. 992-998; 2003.

Naslund et al.; 'Prandial Subcutaneous Injection of Glucagon-Like Peptide'; Br. J. Nutr.; V. 91; pp. 439-446; 2004.

Renshaw et al. 'Peptide YY: A Potential Therapy for Obesity'; Current Drug Targets; V. 6; pp. 171-179; 2005.

Verdich et al. 'A Meta-Analysis of the Effect of Glucagon-Like-Peptide-1 (7-36) Amide on ad Libitum Energy Intake in Humans'; J. Clin. Endocrinal. Metab. V. 86; pp. 4382-4389; Sep. 2001.

Wynne et al.; 'Subcutaneous Oxyntomodulin Reduces Body Weight in Overweight and Obese Subiects: A Double-Blind Randomized, Controlled Trial': Diabetes; V. 54; pp. 2390-2395; 2005.

BIB Bioenterics Intragastric Balloon Program, 'Take Control of Your Weight and Your Life/The Solution for You,' Inamed Health, pp. 1-2; Jan. 19, 2004.

BIB Bioenterics Intragastric Balloon Program, 'Taking the Next Step/Take Control of Your Weight and Your Life,' Inamed Health, pp. 1-9; Apr. 29, 2004.

BIB Data Sheet Directions for Use, 'BioEnterics Intragastric Balloon System,' Inamed Health, 1-12 pp., Feb. 2005.

'Living With the Bib/BioEnterics Intragastric Balloon Program,' Inamed Health; 1-10 Patient Information Brochure; pp.; May 1, 2005.

\* cited by examiner

ARTICULATED GASTRIC IMPLANT CLIP

RELATED APPLICATIONS

The present application claims priority under 35 U.S.C. §119 to U.S. Provisional Application No. 61/485,009, filed May 11, 2011 and U.S. Provisional Application No. 61/394,592, filed Oct. 19, 2010.

FIELD OF THE INVENTION

The present invention is directed to intragastric devices used for the treatment of obesity, and in particular to devices and systems for placement in the stomach cavity.

BACKGROUND OF THE INVENTION

Over the last 50 years, obesity has been increasing at an alarming rate and is now recognized by leading government health authorities, such as the Centers for Disease Control (CDC) and National Institutes of Health (NIH), as a disease. In the United States alone, obesity affects more than 60 million individuals and is considered the second leading cause of preventable death. Worldwide, approximately 1.6 billion adults are overweight, and it is estimated that obesity affects at least 400 million adults.

Obesity is caused by a wide range of factors including genetics, metabolic disorders, physical and psychological issues, lifestyle, and poor nutrition. Millions of obese and overweight individuals first turn to diet, fitness and medication to lose weight; however, these efforts alone are often not enough to keep weight at a level that is optimal for good health. Surgery is another increasingly viable alternative for those with a Body Mass Index (BMI) of greater than 40. In fact, the number of bariatric surgeries in the United States is projected to reach approximately 400,000 annually in 2010.

Examples of surgical methods and devices used to treat obesity include the LAP-BAND® (Allergan Medical of Irvine, Calif.) gastric band and the LAP-BAND AP® (Allergan). However, surgery might not be an option for every obese individual; for certain patients, non-surgical therapies or minimal-surgery options are more effective or appropriate.

Intragastric balloons are also well known in the art as a means for treating obesity. One such inflatable intragastric balloon is described in U.S. Pat. No. 5,084,061 and is commercially available as the Orbera® System from Allergan Medical of Irvine, Calif. These devices are designed to provide therapy for moderately obese individuals who need to shed pounds in preparation for surgery, or as part of a dietary or behavioral modification program. The Orbera® System intragastric balloon floats freely in the stomach cavity and takes up space to reduce the volumetric capacity therein and increase a feeling of satiety, or fullness.

A space-occupying device for the stomach cavity that is fixed in relation to the stomach is seen in U.S. Pat. No. 7,214,233 to Gannoe, et al. One embodiment shown in FIG. 5 includes a toroidal balloon inside the stomach in conjunction with a spherical balloon outside the stomach that are locked together across a gastric wall.

Other methods for treating obesity include convention stomach stapling procedures which can be done surgically or laparoscopically. A number of similar gastric volume reduction devices are disclosed in U.S. Pat. No. 7,510,559 to Deem, et al., which includes creating a small pouch within the stomach from an area of the interior lining thereof. The pouch can be fastened such as with staples rendering it relatively permanent, or the tissue may be excised or pressure necrosis may cause the tissue to simply fall off from the rest of interior surface and be passed normally through the rest of the patient's body.

Despite many advances in the design of intragastric obesity treatment devices, there remains a need for improved devices that can be implanted for longer periods than before or otherwise address certain drawbacks of intragastric balloons and other such implants.

SUMMARY OF THE INVENTION

The present invention addresses the above-described problems by providing passive intragastric apparatuses and methods for inducing satiety and therefore treating obesity. Such passive devices do not autonomously change shape, but instead react within the stomach to induce satiety. The devices includes members that reside within the stomach and pinch or plicate the stomach wall, thus influencing the shape of the stomach.

One embodiment described herein is an intragastric obesity treatment implant comprising a gastric clip formed by a plurality of solid articulated links including two equal rows of links joined by a hinge link. Latching members are provided on the links on the free ends of the gastric clip opposite the hinge link so as to form two parallel rows joined at both ends by, respectively, the hinge link and the latching members. Each articulated link pivotally connects to an adjacent link so as to prevent relative rotation in one direction from linear alignment but permit rotation in a common plane in the other direction. Each link further includes a cam rotatably mounted therein, the cam rotating about longitudinal axes relative to the row of links that lies in the common plane, and opposed cams being configured to non-destructively clamp tissue therebetween. The implant is capable of being unfolded open about the hinge link into a substantially linear delivery configuration and being formed of a material that will resist degradation over a period of at least six months within the stomach.

Desirably, each of the cams has a substantially D-shaped cross-section with a flat side facing the opposite row of links, and the flat side of each cam may have a track-like texture. Each cam may be made of an elastomeric material that is softer than the material of the remainder of the corresponding articulated link. The parallel rows of links are preferably arranged such that when the latching members are engaged opposed cam members are spaced apart a distance between about 4 and 10 mm.

In one embodiment, each of the cams rotatably mounts within a housing, and each of the housings is pivotally connected to either an adjacent housing or the hinge link, and wherein the substantially linear delivery configuration defines a longitudinal direction along the series of articulated links with the axes of rotation of the cams being parallel to the longitudinal direction. Further, each housing may include a protrusion or recess on an outer side that nests within a corresponding protrusion or recess within an outer side of an adjacent housing, and wherein the adjacent housings pivot about hinge pins connecting the corresponding protrusions and recesses. Desirably, the cams face inward and the housings face outward, and the housings have smooth convex exteriors.

Another aspect of the invention is an intragastric obesity treatment implant comprising a gastric clip formed by a plurality of solid articulated links including two equal rows of links joined by a hinge link. Latching members are provided on the links on the free ends of the gastric clip opposite the hinge link so as to form two parallel rows joined at both ends by, respectively, the hinge link and the latching members. Each link further includes a cam rotatably mounted therein about longitudinal axes aligned with the rows of links, and opposed cams are configured to non-destructively clamp tissue therebetween. Each of the cams has a substantially D-shaped cross-section with a flat side facing the opposite row of links. The implant is capable of being unfolded open about the hinge link into a substantially linear delivery configuration and being formed of a material that will resist degradation over a period of at least six months within the stomach. The flat side of each cam may have a track-like texture. Desirably, the parallel rows of links are arranged such that when the latching members are engaged opposed cam members are spaced apart a distance between about 4 and 10 mm. Each cam is preferably made of an elastomeric material that is softer than the material of the remainder of the corresponding articulated link.

In one embodiment, each of the cams rotatably mounts within a housing, and each of the housings is pivotally connected to either an adjacent housing or the hinge link, and wherein the substantially linear delivery configuration defines a longitudinal direction along the series of articulated links with the axes of rotation of the cams being parallel to the longitudinal direction. Further, each housing may include a protrusion or recess on an outer side that nests within a corresponding protrusion or recess within an outer side of an adjacent housing, and wherein the adjacent housings pivot about hinge pins connecting the corresponding protrusions and recesses. Desirably, the cams face inward and the housings face outward, and the housings have smooth convex exteriors.

A method of plicating an inner stomach wall is also disclosed. The method includes providing a gastric clip including a plurality of articulated links hingedly connected and forming two rows of the same number of links joined by a hinge link. The gastric clip includes latching members on the free ends of the two rows of links opposite the hinge link so as to form two parallel rows joined at both ends by, respectively, the hinge link and the latching members. Each link further includes a cam rotatably mounted therein about longitudinal axes aligned with the rows of links, and opposed cams being configured to non-destructively clamp tissue therebetween, the rotatably mounted cams permitting some relatively movement of stomach tissue between the two parallel rows of links. The method includes unfolding the gastric clip about the hinge link into a substantially linear delivery configuration, delivering the unfolded gastric clip transorally through a delivery tube into a patient's stomach, and expelling the gastric clip from the delivery tube. The gastric clip is then folded about the hinge link to encompass a portion of the inner stomach wall between the two rows of links, and the latching members are engaged to plicate the portion of the inner stomach wall between the two parallel rows of links.

Each articulated link in the two parallel rows of links may be pivotally connected to an adjacent link so as to permit rotation in only one direction relative to the adjacent link and create two parallel jaws that won't bow apart. Preferably, each of the cams has a substantially D-shaped cross-section with a flat side facing the opposite row of links. Each of the cams may mounted for rotation within a housing such that the cams face inward and the housings face outward, and wherein the housings have smooth convex exteriors. Desirably, each cam is made of an elastomeric material that is softer than the material of the remainder of the corresponding articulated link.

A further understanding of the nature and advantages of the invention will become apparent by reference to the remaining portions of the specification and drawings.

BRIEF DESCRIPTION OF THE DRAWINGS

Features and advantages of the present invention will become appreciated as the same become better understood with reference to the specification, claims, and appended drawings wherein:

DETAILED DESCRIPTION OF THE PREFERRED EMBODIMENTS

The present invention is directed to an intragastric device that passively treats obesity by reducing space within the stomach to induce feelings of satiety. The term "passive" refers primarily to a device that cannot affect change or stimulate the stomach, but rather one that may do so as a reaction to stomach movement.

Figure 1:
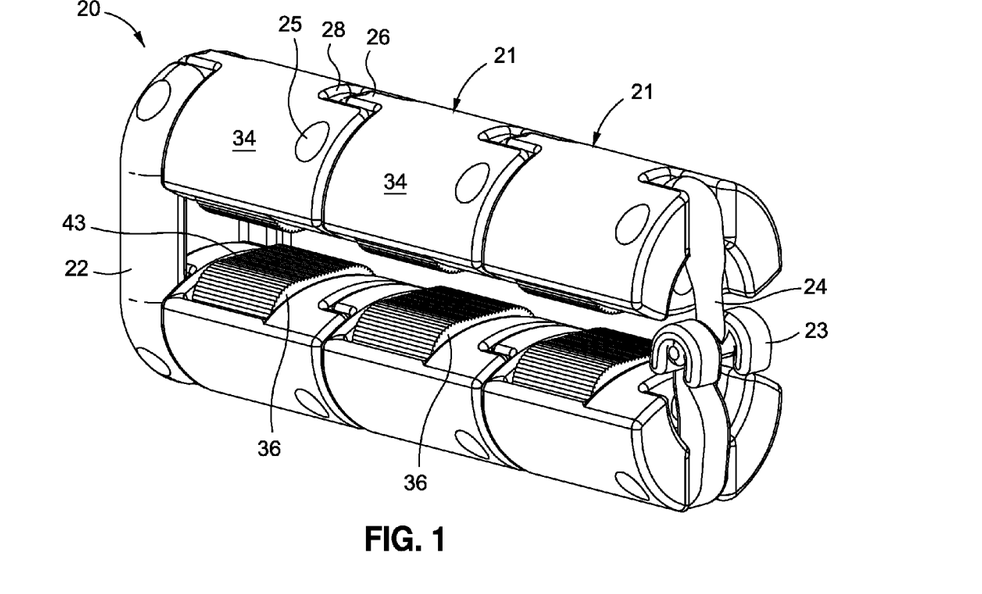
FIG. 1 is a perspective view of an intragastric clip for altering the size of the stomach from within.
Figure 1A:
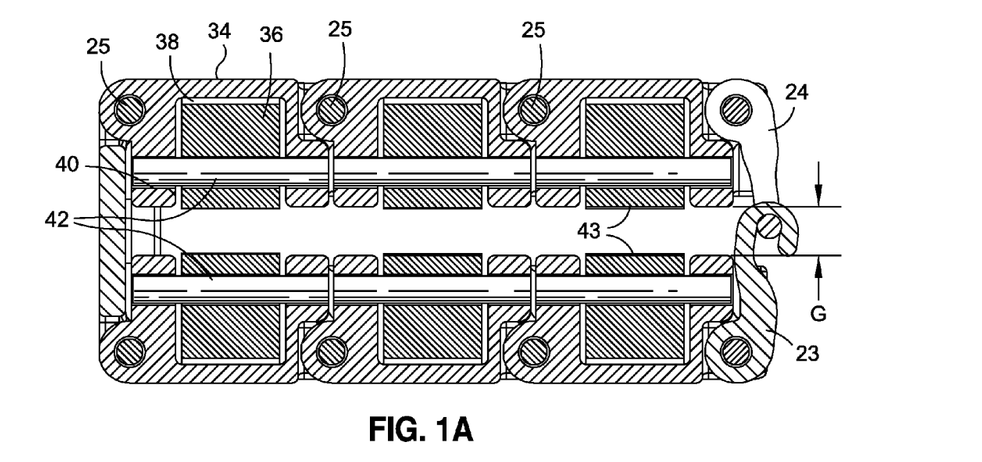
FIG. 1A is a longitudinal sectional view thereof.
Figures 1B, 2:
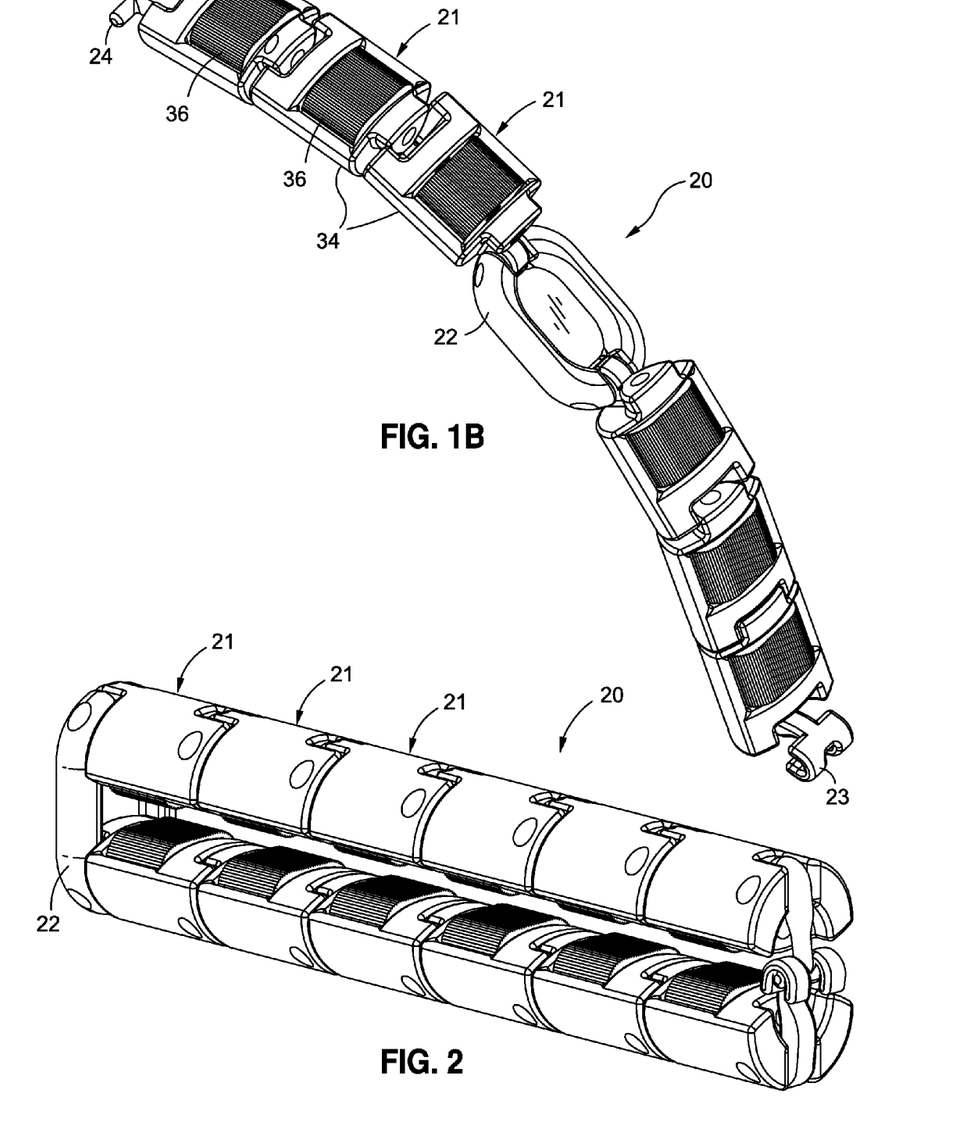
FIG. 1B is a perspective view of the intragastric clip of FIG. 1 shown in an open configuration suitable for delivery to the stomach.
FIG. 2 is a perspective view of an alternative intragastric clip similar to that in FIG. 1 but longer.
Figure 3A:
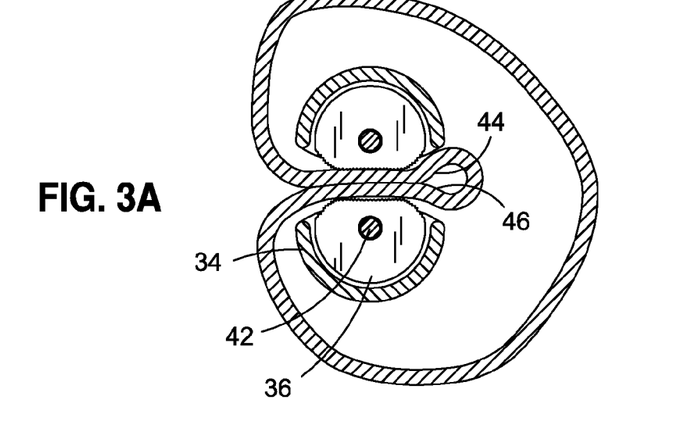
FIGS. 3A-3C illustrate cross-sectional views of the articulated gastric clip of FIG. 1 in a folded state clamping the inside stomach walls with clamping cams alternately unengaged and engaged due to peristaltic forces.
Figure 3B:
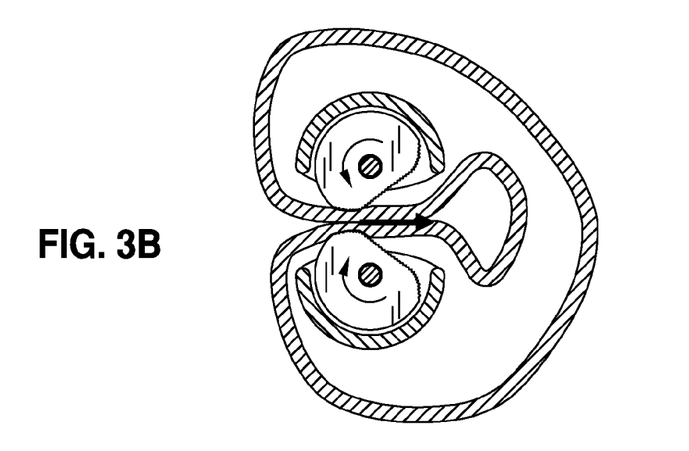
Figure 3C:
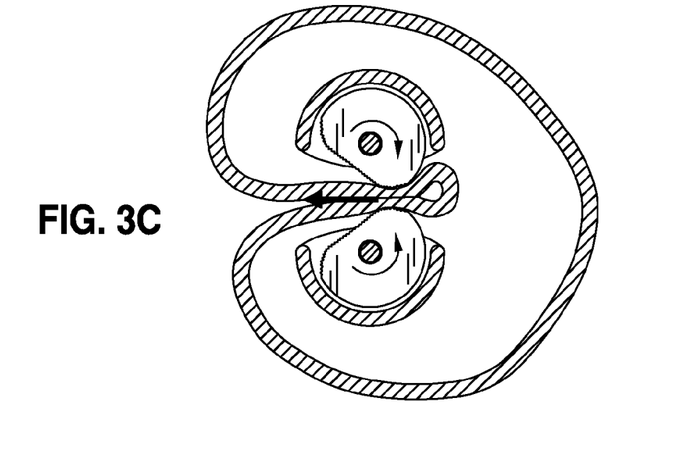

A device 20 in accordance with the present invention that influences the shape of the stomach is seen in FIGS. 1-3 and includes members that pinch or plicate the stomach wall. FIG. 1 illustrates an articulated gastric clip 20 in a closed state. As shown, the articulated gastric clip 20 includes a series of articulated links 21 arranged in two equal rows connected by a hinge link 22. The two links 21 opposite the hinge link 22 include either a mating hook 23 or a latch 24. As seen in the longitudinal sectional view of FIG. 1A, each link 21 hingedly connects to the adjacent links, or at the ends to the hinge link 22, mating hook 23, or mating latch 24, via one or more lateral hinge pins 25. The rows of links 21 extend in a longitudinal direction while the hinge pins 25 are oriented perpendicular thereto so that the various articulated elements may pivot with respect to one another in a single plane.

Each link 21 pivotally connects and is nested to an adjacent link so as to prevent relative rotation in one direction from a linear alignment but permit rotation in the other direction. That is, each link 21 includes a small longitudinal protrusion 26 that nests within a similarly shaped receptacle 28 on the outside of each pair of adjacent links. The hinge pins 25 pass laterally through the nested protrusions 26 and receptacles 28 and their position permits each adjacent pair of links 21 to rotate outward, away from the opposite row of links. That is, the bodies of the links 21 contact each other on the inside thereof to prevent the opposite rotation. Only at the hinge link 22 can the rows rotate toward each other. In this way, the two rows of links 21 can be brought together to form two jaws without bowing apart.

The articulated gastric clip 20 is used to plicate the stomach wall nondestructively (no puncturing through gastric wall) such that the overall volume of the stomach is reduced. The articulated gastric clip 20 may have a customizable length such that the physician may add or remove links 21, or may select from a collection of different length clips.

FIG. 1B shows the assembly of links 21 pivoted open about the hinge link 22 to form more of an elongated chain, suitable for delivery to and removal from the stomach through a transoral tube. The pivoting of the articulated links 21 advantageously promotes easy implantation into and removal out of the patient's stomach region. In one aspect, while in an unfolded state, the articulation feature of the articulated links 21 may allow the articulated gastric clip 20 to travel flexibly through the patient's mouth, down the patient's esophagus and into the patient's stomach in a non-linear fashion, adaptable to the configuration of the patient's openings within the mouth, esophagus and stomach.

With reference back to FIGS. 1 and 1A, each of the articulated links 21 comprises a cam housing 34 and a cam 36. The cam housings 34 desirably have smooth convex exteriors to prevent damage to internal tissue, and include the overlapped protrusions 26 and receptacles 28 in which the hinge pins 25 are journaled. Each cam housing 34 provides a recess 38 in which a cam 36 is journaled for rotation. Specifically, housing walls flanking the recess 38 provide pivot holes 40 for cam shafts 42 on which the cams 36 rotate. That is, either the cams 36 are affixed to the cam shafts 42 which rotate in the pivot holes 40, or the cam shafts are fixed in the holes and the cams rotate thereon. Each link 21 has its own cam shaft 42 so that the links may be articulated independently, and each cam 36 rotates independently of the others. Each cam 36 includes a relatively flat clamping surface 43 that engages stomach wall tissue, and may include features to prevent slippage including (but not limited to) the track-like texture as shown in FIG. 1, other surface textures, surface coatings, and more aggressive cam geometries. Each cam 36 in cross-section has a rounded "D-shape" with lobes defined on both sides of the flat clamping surface 43 and a convex backside. The cams 36 can be made from materials including (but not limited to) rubbers, fluorosilicones, fluoroelastomers, thermoplastic elastomers, thermoplastics, thermosets, metals, glass, or any combinations thereof. In one embodiment, the cams 36 are made of an elastomer material that is gentle on stomach tissue and is softer than the material of the remainder of the links 21, such as the cam housings 34.

In the embodiment illustrated in FIG. 1 the articulated gastric clip 20 includes six articulated links 21, three on either side of the hinge link 22 to form two opposed rows of three links. However, any even number of articulated links 21 may be used, such as six on either side of the hinge link 22 as seen in FIG. 2. Furthermore, multiple clips may be separately deployed within the stomach at any one time. Each gastric clip 20 desirably includes an even number of articulated links 21 so that each has a facing link when the articulated gastric clip 20 is in a folded state. That is, in the folded state, each articulated link 21 lines up across another link to enable clamping of tissue therebetween. More particularly, the cam 36 of each of the articulated links 21 faces a corresponding cam 36 of a different articulated link 21.

The separation gap G seen in FIG. 1A between the cams 36 of an articulation link pair is designed to clamp stomach wall tissue, and may be variable by providing a spring bias, for example. That is, for example, the cam 36 may be spring loaded within the housings 34 such as via the journal mount of the cam shafts 42. In this way, a particular gap G may be a minimum with the springs accommodating some larger thicknesses. Preferably the pressure applied to the stomach wall tissue by the opposed rows of cams 36 is less than that which would cause necrosis, as the gastric clip 20 is intended to be non-destructive. Stomach wall thicknesses vary, and thus the gastric clip 20 may be provided in different sizes with different gaps G, not just in different lengths. A possible range of gaps G is between about 4 and 10 mm.

FIG. 1 illustrates the articulated gastric clip 20 fully folded with retaining hook 23 engaged with the retaining latch 24. In this state, the cams 36 are facing each other at their closest distance, which is sufficient to plicate an inner wall of the patient's stomach thereby causing the effective volume of the patient's stomach to be reduced. The design of the articulated gastric clip 20 is such that each articulated link 21 may rotate about 90° outward from the flat state shown in FIG. 1A.

In another aspect, as shown in FIG. 1A, when each articulated link 21 is in a flat state and paired, facing another articulated link 21, the retaining latch 24 may be received and engaged by the retaining hook 23 to keep the articulated gastric clip 20 in a folded state. Part of either the hook 23 or the latch 24 can be made from an elastomeric material, which will allow for some forgiveness when opening and closing the device. The clasp closure may be made from materials including (but not limited to) rubbers, fluorosilicones, fluoroelastomers, thermoplastic elastomers, thermoplastics, thermosets, metals, glass, or any combinations thereof. Unless the retaining latch 24 and the retaining hook 23 are carefully disengaged (e.g., by using a standard grabber), any outward pressure to "unfold" the articulated gastric clip 20 may only tighten the engagement between the retaining latch 24 and the retaining clip 23. Of course, other fasteners or clasps than the hook 23 and latch 24 arrangement are contemplated, such as a barbed finger passing through an aperture, a zip-tie like closure, etc.

In one aspect, the rotation of the cams 36 advantageously allow for the stomach to contract and digest food and function normally without tearing or puncturing of the inner stomach walls, while effectively reducing the volume of the stomach by not becoming disengaged completely from the inner stomach walls.

FIG. 3A-3C illustrate cross sections of the links 21 with the inner stomach of the patient engaged, and show the process by which the cam mechanism operates to hold the inner stomach of the patient in place between the cams 36 while permitting some relative movement. FIG. 3A shows an example of one articulated pair including two cams 36. As described, the cams 36 are housed in cam housings 34 and each pivots about cam shaft 42. The stomach includes a first portion 44 and a second portion 46 that have been clamped between the cams 36 to reduce the effective volume of the stomach. The configuration of FIG. 3A may be achieved when the articulated gastric clip 20 is in a folded state with the retaining latch 24 engaged and held by the retaining hook 23 with the stomach plicated inside the formed gap of the articulated gastric clip, and specifically when held between the facing clamping surfaces 43 of facing cams 36.

When the stomach walls move (e.g., during stomach contractions when the patient is eating), the first portion 44 and the second portion 46 may begin to shift positions. However, the cams 36 act in concert to prevent slipping. As the stomach wall is pulled through the device (in either direction), the cams will tend to rotate and resist further slippage. The cams are designed such that any rotation (clockwise or counterclockwise) from their baseline orientation will bring the cam lobes closer and reduce the distance between the cams, effectively tightening their grip on the material being held.

FIG. 3B illustrates the first portion 44 and the second portion 46 of stomach having moved to the right in the direction of the unnumbered arrow from stomach movement. As the first portion 44 and the second portion 46 of stomach move "inwards" or in a direction effectively reducing the volume of stomach, the cams 36 pivot about cam shaft 42 as shown by rotation arrows since the cams 36 are in contact with the first and second portions 44 and 46. Accordingly, when the lobes of cams 36 come into very close proximity with each other as shown, the first and second portions 44 and 46 of the stomach are prevented from further movement in that same direction. At this position, the first portion 44 and the second portion 46 of stomach may remain stationary or shift in the opposite direction, "outward" or in a direction effectively increasing the volume of the stomach.

FIG. 3C illustrates an "outward" direction of the shift (as shown by the unnumbered arrow to the left) of the first portion 44 and the second portion 46 of stomach. As the first portion 44 and the second portion 46 of stomach move "outwards" or in a direction effectively increasing the volume of stomach, the cams 36 pivot in the other direction about cam shaft 42 as indicated. Accordingly, when the other lobes of cams 36 (as compared to FIG. 3B) come into very close proximity with each other as shown, the first and second portions 44, 46 of the stomach are prevented from further movement in that same "outward" direction.

As shown by FIG. 3A-3C, the cams 36 may rotate freely in between the positions shown in FIG. 3B and FIG. 3C in response to the shifting of the plicated portion of the inner stomach walls. However, regardless of the position of the cams 36, the inner stomach walls are always held between them in a non-destructive manner. In this way, the articulated gastric clip 20 remains engaged with the inner stomach walls when in a folded position, plicating the stomach walls.

As mentioned, the links 21 may articulate about their pin connections by at least 90°. This facilitates insertion and removal procedures. The linkages can be rigid or semi-rigid and range in length from 5 mm to 40 mm, and may be manufactured from materials including (but not limited to) rubbers, fluorosilicones, fluoroelastomers, thermoplastic elastomers, thermoplastics, thermosets, metals, glass, or any combinations thereof. The materials discussed herein advantageously allow the cams 36 to withstand the acidic environment of the patient's stomach for at least six months, and preferably more than 1 year.

Although the invention has been described and illustrated with a certain degree of particularity, it is understood that the present disclosure has been made only by way of example, and that numerous changes in the combination and arrangement of parts can be resorted to by those skilled in the art without departing from the scope of the invention, as hereinafter claimed.

What is claimed is:

1. An intragastric obesity treatment implant, comprising:
a gastric clip comprising a plurality of solid articulated links including two equal rows of links joined by a hinge link, wherein latching members are provided on the links on the free ends of the gastric clip opposite the hinge link so as to form two parallel rows joined at both ends by, respectively, the hinge link and the latching members, the two parallel rows being parallel to a longitudinal axis, each articulated link being pivotally connected to an adjacent link so as to prevent relative rotation from linear alignment in a direction away from the longitudinal axis, but permit relative rotation from linear alignment in a direction toward the longitudinal axis, each link further including a cam rotatably mounted therein, each cam rotating about a longitudinal axis relative to the row of links in which the cam is mounted, and opposed cams being configured to non-destructively clamp tissue therebetween,
the implant being capable of being unfolded open about the hinge link into a substantially linear delivery configuration and being formed of a material that will resist degradation over a period of at least six months within the stomach.

2. The implant of claim 1, wherein each of the cams has a substantially D-shaped cross-section with a flat side facing the opposite row of links.

3. The implant of claim 2, wherein the flat side of each cam has a track-like texture.

4. The implant of claim 1, wherein each cam is made of an elastomeric material that is softer than the material of the remainder of the corresponding articulated link.

5. The implant of claim 1, wherein the parallel rows of links are arranged such that when the latching members are engaged opposed cam members are spaced apart a distance between about 4 and 10 mm.

6. The implant of claim 1, wherein each of the cams is mounted for rotation within a housing, and each of the housings is pivotally connected to either an adjacent housing or the hinge link, and wherein the substantially linear delivery configuration defines a longitudinal direction along the series of articulated links with the axes of rotation of the cams being parallel to the longitudinal direction.

7. The implant of claim 1, wherein each of the cams is mounted for rotation within a housing, and each of the housings is pivotally connected to either an adjacent housing or the hinge link, and wherein each housing includes a protrusion or recess on an outer side that nests within a corresponding protrusion or recess within an outer side of an adjacent housing, and wherein the adjacent housings pivot about hinge pins connecting the corresponding protrusions and recesses.

8. The implant of claim 1, wherein each of the cams is mounted for rotation within a housing such that the cams face inward and the housings face outward, and wherein the housings have smooth convex exteriors.

9. An intragastric obesity treatment implant, comprising:
a gastric clip comprising a plurality of solid articulated links including two equal rows of links joined by a hinge link, wherein latching members are provided on the articulated links on the free ends of the gastric clip opposite the hinge link so as to form two parallel rows joined at both ends by, respectively, the hinge link and the latching members, each link further including a cam rotatably mounted therein about longitudinal axes aligned with the rows of links, each of the cams has a substantially D-shaped cross-section with a flat side facing the opposite row of links, and opposed cams being configured to non-destructively clamp tissue therebetween,
the implant being capable of being unfolded open about the hinge link into a substantially linear delivery configuration and being formed of a material that will resist degradation over a period of at least six months within the stomach.

10. The implant of claim 9, wherein the flat side of each cam has a track-like texture.

11. The implant of claim 9, wherein the parallel rows of links are arranged such that when the latching members are engaged opposed cam members are spaced apart a distance between about 4 and 10 mm.

12. The implant of claim 9, wherein each of the cams is mounted for rotation within a housing, and each of the housings is pivotally connected to either an adjacent housing or the hinge link, and wherein the substantially linear delivery configuration defines a longitudinal direction along the series of articulated links with the axes of rotation of the cams being parallel to the longitudinal direction.

13. The implant of claim 9, wherein each of the cams is mounted for rotation within a housing, and each of the housings is pivotally connected to either an adjacent housing or the hinge link, and wherein each housing includes a protrusion or recess on an outer side that nests within a corresponding protrusion or recess within an outer side of an adjacent housing, and wherein the adjacent housings pivot about hinge pins connecting the corresponding protrusions and recesses.

14. The implant of claim 9, wherein each of the cams is mounted for rotation within a housing such that the cams face inward and the housings face outward, and wherein the housings have smooth convex exteriors.

15. The implant of claim 9, wherein each cam is made of an elastomeric material that is softer than the material of the remainder of the corresponding articulated link.

16. A method of plicating an inner stomach wall, comprising:
providing a gastric clip including a plurality of articulated links hingedly connected and forming two rows of the same number of links joined by a hinge link, the gastric clip further including latching members on the free ends of the two rows of links opposite the hinge link so as to form two parallel rows joined at both ends by, respectively, the hinge link and the latching members, the two parallel rows being parallel to a longitudinal axis, each articulated link being pivotally connected to an adjacent link so as to prevent relative rotation from linear alignment in a direction away from the longitudinal axis, but permit relative rotation from linear alignment in a direction toward the longitudinal axis, each link further including a cam rotatably mounted therein, each cam rotating about a longitudinal axis relative to the row of links in which the cam is mounted, and opposed cams being configured to non-destructively clamp tissue therebetween;
unfolding the gastric clip about the hinge link into a substantially linear delivery configuration;
delivering the unfolded gastric clip transorally through a delivery tube into a patient's stomach;
expelling the gastric clip from the delivery tube;
folding the gastric clip about the hinge link and encompassing a portion of the inner stomach wall between the two rows of links; and
engaging the latching members to plicate the portion of the inner stomach wall between the two parallel rows of links, the rotatably mounted cams permitting some relatively movement of stomach tissue between the two parallel rows of links.

17. The method of claim 16, wherein each articulated link in the two parallel rows of links is pivotally connected to an adjacent link so as to permit rotation in only one direction relative to the adjacent link and create two parallel jaws that won't bow apart.

18. The method of claim 16, wherein each of the cams has a substantially D-shaped cross-section with a flat side facing the opposite row of links.

19. The method of claim 16, wherein each of the cams is mounted for rotation within a housing such that the cams face inward and the housings face outward, and wherein the housings have smooth convex exteriors.

20. The method of claim 19, wherein each cam is made of an elastomeric material that is softer than the material of the remainder of the corresponding articulated link.

21. An intragastric device for treatment of obesity, comprising:
a clip comprising a plurality of articulated links including a plurality of rows of links joined by a hinge link, wherein latching members are provided on the links on the free ends of the clip opposite the hinge link so as to form a plurality of rows joined at both ends by, respectively, the hinge link and the latching members, the rows spaced from each other and a longitudinal axis therebetween, each articulated link being connected to an adjacent link so as to prevent relative rotation from linear alignment away from the longitudinal axis, but permit relative rotation from linear alignment toward the longitudinal axis, each link further including a cam rotatably mounted therein, the implant being capable of being unfolded open about the hinge link into a substantially linear configuration.

* * * * *